United States Patent [19]

Kamishita et al.

[11] 4,267,169

[45] May 12, 1981

[54] NOVEL PREPARATION OF CLOTRIMAZOLE

[75] Inventors: Takuzo Kamishita; Kazuhiko Kamishita, both of Takatsuki, Japan

[73] Assignee: Toko Yakuhin Kogyo Kabushiki Kaisha, Osaka, Japan

[21] Appl. No.: 56,978

[22] Filed: Jul. 12, 1979

[30] Foreign Application Priority Data

Jul. 22, 1978 [JP] Japan .................................. 53-89787
Jul. 22, 1978 [JP] Japan .................................. 53-89788
Jul. 22, 1978 [JP] Japan .................................. 53-89789

[51] Int. Cl.³ .................. A61K 31/74; A61K 31/415; A61K 31/165
[52] U.S. Cl. ................................ 424/78; 424/273 R; 424/358; 424/324
[58] Field of Search .................... 424/273 R, 358, 81, 424/78, 324

[56] References Cited

U.S. PATENT DOCUMENTS 3,660,576  5/1972  Buchel et al. .................... 424/273 R
3,660,577  5/1972  Buchel et al. .................... 424/273 R Primary Examiner—Delbert R. Phillips
Assistant Examiner—Blondel Hazel
Attorney, Agent, or Firm—Stevens, Davis, Miller & Mosher

[57] ABSTRACT

A new type of preparation of clotrimazole, such as gel preparation, creamy preparation and liquid preparation, which are useful for an external use for the treatment of various trichophytoses, wherein the active clotrimazole is contained as being dissolved in crotamiton. Said new type of preparation of clotrimazole can be applied to the skin without drawbacks such as skin irritation and soiling of clothes as seen in the conventional tincture or ointments.

13 Claims, No Drawings

NOVEL PREPARATION OF CLOTRIMAZOLE

The present invention relates to a new type of preparation of clotrimazole, more particularly, novel gel preparation, creamy preparation and liquid preparation which are useful for an external use, and a method for the preparation of the same.

It is well known that clotrimazole, i.e. 1-[(2-chlorophenyl)diphenylmethyl]-1H-imidazole (molecular formula: $C_{22}H_{17}ClN_2$, molecular weight: 344.85, melting point: 142°–145° C.), has excellent antifungal activities and is useful for the treatment of various trichophytoses, such as trichophytia pompholyciformis, tinea trichophytina, and trichophytia maculovesiculosa. Since clotrimazole is water-insoluble, it is usually used in the form of a tincture or an ointment. However, in case of a tincture, the solvent is readily evaporated when applied onto a skin, and hence, clotrimazole precipitates on the skin, which results in insufficient absorption and insufficient therapeutic effect. Moreover, since the tincture contains no water, it gives strong irritation like causalgia to the applied skin, and further, owing to the high fluidity, it has an inferior spreading properties and it flows down from the applied skin, which result in precipitation and insufficient absorption of the active ingredient. On the other hand, ointments feel sticky and unpleasant when applied to the skin, and further, the active ingredient is insufficiently absorbed from the skin. Moreover, the applied surface is rubbed with clothes, which results in loss of the active ingredient and also soiling of clothes.

In order to overcome the drawbacks of the conventional tincture and ointment, the present inventors have intensively studied to find a new type of preparation of clotrimazole. As a result, it has been found that clotrimazole is easily soluble in crotamiton (i.e. N-crotonyl-N-ethyl-o-toluidine) and the solution of clotrimazole in crotamiton is very useful for preparing a new type of preparation of clotrimazole, such as a gel preparation, creamy preparation and liquid preparation.

Although clotrimazole is white crystalline powder and is easily soluble in ethanol, chloroform, carbon tetrachloride, it is insoluble in water and ether, and chloroform and carbon tetrachloride can not be used as a solvent for a medicine from the viewpoint of toxicity. Ethanol can be used as a solvent, but the tincture using ethanol has drawbacks as mentioned above. On the contrary, crotamiton is excellent as a solvent for clotrimazole, because crotamiton is also useful as a medicine and hence there is no problem of toxicity. The solution of clotrimazole in crotamiton is admixed with pharmaceutically acceptable carriers or diluents to give the desired preparations. The solution alone can not be used, because it does not contain water and shows less penetration into the skin which results in less absorption of the active ingredient.

An object of the present invention is to provide a new type of preparation of clotrimazole which is useful for external use. Another object of the invention is to provide a gel preparation of clotrimazole. A further object of the invention is to provide a creamy preparation of clotrimazole. A further object of the invention is to provide a liquid preparation of clotrimazole. Still further object of the invention is to provide a process for preparing the preparations as set forth above. These and other object of the invention will be apparent from the following description.

The preparations of the present invention can be prepared by dissolving clotrimazole in crotamiton, and admixing the solution of clotrimazole in crotamiton with pharmaceutically acceptable carriers or diluents.

The external gel preparation is a transparent preparation having a pH of 4 to 10 and a viscosity of 2,000 to 100,000 cps at 20° C., which is prepared by admixing a solution of clotrimazole in crotamiton with ethanol which may contain less than 40% by weight, preferably 5 to 30% by weight, of propylene glycol, and an aqueous solution of a carboxyvinyl polymer, and thereto adding with stirring a basic substance. In the gel preparation, crotamiton is contained in an amount of 2 to 10% by weight based on the total amount of the preparation. Ethanol or propylene glycol-containing ethanol is added so that the solution of clotrimazole in crotamiton can be admixed with water with keeping the transparency thereof. Ethanol includes also denatured ethanol. Ethanol or propylene glycol-containing ethanol is added in an amount of 30 to 70% by weight, preferably 40 to 60% by weight, based upon the total weight of the preparation. When the amount of the ethanol is lower than 30% by weight, crotamiton is not sufficiently admixed with water and hence the preparation is separated into two phases and the transparency is lost. On the other hand, when the amount is over 70% by weight, ethanol tends to evaporate and the preparation becomes unstable, and further, the preparation gives undesirably irritation to the skin when applied. When propylene glycol is used together with ethanol, the evaporation of ethanol is inhibited and hence the stability of the preparation is enhanced. Moreover, propylene glycol has an effect of improving moisture retention when applied and of promoting the penetration of the active ingredient into the skin. Propylene glycol is admixed in an amount of less than 40% by weight with ethanol. The amount of propylene glycol in the preparation is preferably in the range of 5 to 30% by weight based upon the total weight of the preparation.

To the gel preparation is added a carboxyvinyl polymer in order to give a suitable viscosity to the preparation. The carboxyvinyl polymer is a hydrophilic vinyl polymer with active carboxyl groups which is prepared by polymerization of monomers comprising predominantly acrylic acid [cf. Chem. & Eng. News, Vol. 36, page 64 (Sept. 29, 1958)]. All commercially available carboxyvinyl polymers can be used in the present invention. Suitable examples are Carbopol 934, Carbopol 940 and Carbopol 941, which are tradenames of the products of Goodrich Chemical. The carboxyvinyl polymer has free carboxyl groups and the aqueous solution is acidic. When the carboxyvinyl polymer is neutralized with a basic substance, a sticky gel is formed.

The basic substance to be used for neutralization of carboxyvinyl polymer includes organic amines, such as an alkylamine having 1 to 4 carbon atoms (e.g. methylamine, ethylamine, or propylamine), a dialkylamine having 1 to 4 carbon atoms in each alkyl moiety (e.g. dimethylamine, diethylamine, or dipropylamine), a trialkylamine having 1 to 4 carbon atoms in each alkyl moiety (e.g. trimethylamine, triethylamine, or tripropylamine), an alkanolamine having 1 to 4 carbon atoms in the alkanol moiety (e.g. methanolamine, ethanolamine, or propanolamine), a dialkanolamine having 1 to 4 carbon atoms in each alkanol moiety (e.g. dimethanolamine, diethanolamine, dipropanolamine, or dibutanolamine), a trialkanolamine having 1 to 4 carbon atoms in each alkanol moiety (e.g. trimethanolamine, triethanolamine, tripropanolamine, or tributanolamine), and trimethylolaminomethane, and also includes inorganic bases such as ammonia, an aqueous solution of alkali metal hydroxides (e.g. sodium hydroxide, or potassium hydroxide). All these basic substances can give a gel having a similar viscosity when the aqueous solution of carboxyvinyl polymer is neutralized with the basic substances.

In the preparation of the gel preparation, one part by weight of clotrimazole is firstly dissolved in about 3 parts by weight or more, preferably 4 to 5 parts by weight, of crotamiton at a temperature of lower than 100° C., preferably at about 70° to 80° C. To the resulting solution are added ethanol or a mixture of ethanol and propylene glycol and further an aqueous solution of carboxyvinyl polymer. To the mixture is added with stirring a basic substance. By the addition of the basic substance, the carboxyvinyl polymer is neutralized to increase the viscosity of the mixture, and there is obtained a transparent gel preparation wherein the components are all uniformly dispersed. The gel preparation thus obtained has a viscosity of 2,000 to 100,000 cps, wherein the carboxyvinyl polymer is contained in an amount of 0.1 to 3.0% by weight, preferably 0.5 to 1.2% by weight, based upon the total weight of the preparation. The carboxyvinyl polymer is usually used in the form of a 1 to 5% aqueous solution, and after mixing the aqueous solution of carboxyvinyl polymer with the mixture of the solution of clotrimazole and other components, the content of the carboxyvinyl polymer in the gel preparation is regulated in the above range by adding thereto water. Moreover, the gel preparation is regulated to a pH of 4 to 10, preferably 6 to 9, by controlling the amount of the basic substance. The gel preparation contains usually 0.5 to 2.0% by weight of clotrimazole and 2 to 10% by weight of crotamiton based upon the total weight of the preparation.

The external creamy preparation of the present invention has a pH of 4 to 10 and a viscosity of 10,000 to 100,000 cps at 20° C., which are similar to those of the above gel preparation, but this creamy preparation does not contain ethanol and contains an oily substance and a nonionic surfactant. That is, the creamy preparation of clotrimazole is prepared by adding an oily substance, a nonionic surfactant and an aqueous solution of carboxyvinyl polymer to a solution of clotrimazole in crotamiton, and adding thereto with stirring a basic substance.

By the addition of the oily substance and the nonionic surfactant, the preparation becomes the form of a cream which is uniformly miscible with water.

The oily substance includes higher fatty alcohols having 8 to 18 carbon atoms, such as octyl alcohol, capryl alcohol, nonyl alcohol, lauryl alcohol, myristyl alcohol, cetyl alcohol, or stearyl alcohol; monovalent or divalent fatty acids having 8 to 18 carbon atoms, such as lauric acid, myristic acid, palmitic acid, oleic acid, linoleic acid, sebacic acid, or stearic acid; alkyl esters of the fatty acids as mentioned above wherein the alkyl moiety has 1 to 18 carbon atoms, such as isopropyl myristate, diethyl sebacate, dibutyl sebacate, dioctyl sebacate, or decyl oleate; liquid or solid hydrocarbons, such as liquid paraffin or other various paraffins; fats and oils, such as cacao butter, or lard; and a mixture thereof.

The nonionic surfactant to be incorporated into the creamy preparation includes sorbitan sesquioleate, sorbitan trioleate, sorbitan monooleate, sorbitan monostearate, sorbitan monolaurate, polyethylene glycol monostearate, polyoxyethylene sorbitan monooleate, polyoxyethylene sorbitan monolaurate, polyoxyethylene nonylphenyl ether, polyoxyethylene cetyl ether, polyoxyethylene lauryl ether, or a mixture thereof.

In order to give an appropriate viscosity to the creamy preparation, the same carboxyvinyl polymer as mentioned above is added to this preparation, and further, the same basic substance as mentioned above is also added thereto in order to neutralize the carboxyvinyl polymer, likewise.

In the preparation of the creamy preparation, one part by weight of clotrimazole is firstly dissolved in about 3 parts by weight or more, preferably 4 to 5 parts by weight, of crotamiton at a temperature of lower than 100° C., preferably at about 70° to 80° C. To the solution thus obtained are added an oily substance, a nonionic surfactant and an aqueous solution of carboxyvinyl polymer. After dissolving completely the oily substance, optionally by heating, a basic substance is added to the mixture with stirring. The basic substance may be used in the form of an aqueous solution thereof. By the addition of the basic substance, the carboxyvinyl polymer is neutralized to increase the viscosity of the preparation, and there is obtained a creamy preparation wherein the ingredients are all uniformly contained and clotrimazole is dissolved in crotamiton.

The creamy preparation has a viscosity of 10,000 to 100,000 cps, wherein the carboxyvinyl polymer is contained in an amount of 0.1 to 3.0% by weight, preferably 0.5 to 1.2% by weight, based upon the total weight of the preparation. The carboxyvinyl polymer is usually used in the form of a 1 to 5% aqueous solution, and after mixing the aqueous solution of carboxyvinyl polymer with the mixture of the solution of clotrimazole and other components, the content of the carboxyvinyl polymer in the creamy preparation is regulated in the above range by adding thereto water. Moreover, the creamy preparation is regulated to a pH of 4 to 10, preferably 5 to 8, by controlling the amount of the basic substance.

The creamy preparation contains 0.5 to 2.0% by weight of clotrimazole, 2 to 10% by weight of crotamiton, 10 to 50% by weight of the oily substance, and 0.5 to 5.0% by weight of the nonionic surfactant, based upon the total weight of the preparation. When a solid oily substance such as higher fatty acids is used, the viscosity of the creamy preparation becomes higher, and hence, such a solid oily substance should be used in a smaller amount.

Besides, the creamy preparation may be incorporated with propylene glycol. The propylene glycol is effective for increase of stability of the creamy preparation and also for improving moisture retention when applied and for promoting the penetration of the active ingredient into the skin. The propylene glycol is used in an amount of less than 40% by weight, preferably 5 to 15% by weight, based upon the total weight of the preparation. When propylene glycol is used in an amount of more than 40% by weight, the surface of the skin to which the preparation is applied is sticky and is hardly dried because the formation of film of carboxyvinyl polymer is inhibited by propylene glycol. Moreover, a small amount of sodium edetate (i.e. sodium ethylenediaminetetraacetate) may be added to the creamy preparation in order to increase the stability of carboxyvinyl polymer.

The external liquid preparation is a transparent liquid preparation which is prepared by dissolving one part by weight of clotrimazole in 3 to 5 parts by weight of crotamiton, and adding to the resulting solution ethanol or propylene glycol-containing ethanol and further adding thereto with stirring a purified water.

In the liquid preparation of the present invention, ethanol is contained in an amount of 30 to 60% by weight, preferably 40 to 55% by weight, based upon the total weight of the preparation. When ethanol is contained in an amount of less than 30%, crotamiton contained in the preparation is not uniformly admixed with water and is separated out, and on the other hand, when the amount of ethanol is too large, it gives undesirably irritation onto the skin when applied. The ethanol includes also denatured ethanol, and further, may contain less than 40% by weight, preferably 5 to 30% by weight, of propylene glycol. Propylene glycol is effective for improving moisture retention when the preparation is applied onto the skin and for promoting the penetration of the active ingredient into the skin, and further is also effective for inhibiting the separation of crotamiton and water and also for inhibiting too early drying of the applied preparation.

The liquid preparation contains 0.5 to 2.0% by weight of clotrimazole, 2 to 10% by weight of crotamiton, 30 to 60% by weight of ethanol or propylene glycol-containing ethanol, and about 30 to 70% by weight of purified water, based upon the total weight of the preparation.

The new type of preparation of clotrimazole of the present invention is stable and any crystal does not precipitate during storage thereof or when applied to the skin, and can be applied to the skin in a conventional manner. For instance, a gel preparation having a comparatively low viscosity can directly be applied to the skin from a vessel (e.g. a tube), and on the other hand, the gel preparation and the creamy preparation which have a comparatively higher viscosity can be applied with a finger. In case of the gel preparation and creamy preparation, when they are applied to the skin, they are contacted with salts such as sodium chloride which are contained in a very small amount in the perspiration or are present on the surface of the skin and thereby the viscosity of the preparation is rapidly decreased, and the preparation is liquefied and shows excellent spreadability onto the skin and further a film of carboxyvinyl polymer is formed on the skin, which promotes the absorption of the active ingredient into the skin. Moreover, the film of carboxyvinyl polymer thus formed is readily dried when contacted with air, and hence, the skin surface, to which the preparation is applied, is not sticky and is smooth. Thus, the drawbacks of ointments such as soiling of clothes and bad feeling, can be eliminated. Besides, the gel preparation and creamy preparation of the present invention is very stable and does not have such drawbacks as seen in the conventional ointments, such as melting or liquefaction at summer time and hardening or solidification at winter time and also separation of the oily phase and aqueous phase. The liquid preparation of the present invention contains water and hence can be applied to the skin without such an undesirable irritation as seen in the conventional tincture.

The present invention is illustrated by the following Examples, but is not limited thereto. In the Examples, 99.5% ethanol was used, and the purified water was prepared by purifying water with an ion exchange resin, and the viscosity was measured at 20° C. by a C-type viscosimeter (made by Tokyo Keiki Co., Ltd., Japan).

EXAMPLE 1

Clotrimazole (1 g) was dissolved in crotamiton (4 g) at about 70° to 80° C., and thereto was added ethanol (40 g), and the mixture was stirred to give a uniform solution. To the solution was added a 4% aqueous solution of carboxyvinyl polymer (Carbopol 940) (20 g) with stirring well, and thereto was gradually added a 10% aqueous solution of triethanolamine (10.8 g) and further was added purified water to make 100 g in total. After stirring well, the mixture was cooled to give a transparent gel preparation having a viscosity of 35,000 cps and a pH of 6.85.

EXAMPLE 2

Clotrimazole (1 g) was dissolved in crotamiton (4 g) at about 70° to 80° C. and thereto was gradually added ethanol (40 g) to give a uniform solution. To the solution was added a 4% aqueous solution of carboxyvinyl polymer (Carbopol 940) (7 g) with stirring well, and thereto was gradually added with stirring a 10% aqueous solution of triethanolamine (3.78 g) and further was added purified water to make 100 g in total. After stirring well, the mixture was cooled to give a transparent gel preparation having a viscosity of 11,000 cps and a pH of 6.92.

EXAMPLE 3

Clotrimazole (0.5 g) was dissolved in crotamiton (2 g) at about 70° to 80° C., and thereto was added ethanol (40 g) to give a uniform solution. To the solution was added a 4% aqueous solution of carboxyvinyl polymer (Carbopol 940) (40 g) and thereto was gradually added with well stirring a 20% aqueous solution of monoethanolamine (8 g) and further was added purified water to make 100 g in total. After stirring well, the mixture was cooled to give a transparent gel preparation having a viscosity of 47,000 cps and a pH of 6.79.

EXAMPLE 4

Clotrimazole (2 g) was dissolved in crotamiton (8 g) at about 70° to 80° C., and thereto was added ethanol (40 g) to give a uniform solution. To the solution was added a 4% aqueous solution of carboxyvinyl polymer (Carbopol 940) (20 g) with stirring well, and thereto was gradually added with stirring a 10% aqueous solution of triethanolamine (8 g) and finally added purified water to make 100 g in total. After stirring well, the mixture was cooled to give a transparent gel preparation having a viscosity of 33,000 cps and a pH of 6.82.

EXAMPLE 5

Crotrimazole (1 g) was dissolved in crotamiton (4 g) at about 70° to 80° C., and thereto was gradually added ethanol (40 g) to give a uniform solution. To the solution was added a 1% aqueous solution of carboxyvinyl polymer (Carbopol 940) (15 g) with stirring well, and thereto was gradually added a 10% aqueous solution of diisopropanolamine (2.0 g) and further added purified water to make 100 g in total. After stirring well, the mixture was cooled to give a transparent gel preparation having a viscosity of 2,500 cps and a pH of 8.20.

EXAMPLE 6

Clotrimazole (0.5 g) was dissolved in crotamiton (3 g) at about 70° to 80° C., and thereto was added ethanol (40 g) to give a uniform solution. To the solution was added a 4% aqueous solution of carboxyvinyl polymer (Carbopol 940) (40 g) with stirring well, and thereto was gradually added a 10% aqueous solution of diisopropanolamine (4 g) and further added purified water to make 100 g in total. After stirring well, the mixture was cooled to give a transparent gel preparation having a viscosity of 28,000 cps and a pH of 4.92.

EXAMPLE 7

Clotrimazole (1 g) was dissolved in crotamiton (4 g) at about 70° C., and thereto were added isopropyl myristate (10 g), propylene glycol (10 g), polyoxyethylene sorbitan monolaurate (1 g), a 4% aqueous solution of carboxyvinyl polymer (Carbopol 940) (17 g), purified water (53 g) and a 1% aqueous solution of sodium edetate (1.2 g). The mixture was continuously stirred at about 70 to 80° C. on a water bath, and thereto was added a 2% aqueous solution of sodium hydroxide (2 g) and further added purified water to make 100 g in total. After stirring well, the mixture was cooled to give a creamy preparation having a viscosity of 62,000 cps and a pH of 4.30.

EXAMPLE 8

Clotrimazole (2 g) was dissolved in crotamiton (8 g) at about 70° C., and thereto were added liquid paraffin (10 g), propylene glycol (10 g), polyoxyethylene lauryl ether (1 g), a 4% aqueous solution of carboxyvinyl polymer (Carbopol 940) (20 g), purified water (43 g) and a 1% aqueous solution of sodium edetate (1.2 g). The mixture was heated at about 70° to 80° C. on a water bath, and thereto was added with stirring a 2% aqueous solution of triethanolamine (4.68 g) and further added purified water to make 100 g in total. After stirring well, the mixture was cooled to give a creamy preparation having a viscosity of 66,000 cps and a pH of 4.50.

EXAMPLE 9

Clotrimazole (0.5 g) was dissolved in crotamiton (2 g) with warming, and thereto were added isopropyl myristate (10 g), propylene glycol (10 g), polyoxyethylene sorbitan monostearate (1.5 g), a 4% aqueous solution of carboxyvinyl polymer (Carbopol 940) (17 g), purified water (54 g) and a 1% aqueous solution of sodium edetate (1.2 g). The mixture was heated at about 70° to 80° C. on a water bath, and thereto was added with stirring a 2% aqueous solution of triethylamine (2.95 g) and further added purified water to make 100 g in total. After stirring well, the mixture was cooled to give a creamy preparation having a viscosity of 56,000 cps and a pH of 4.70.

EXAMPLE 10

Clotrimazole (1 g) was dissolved in crotamiton (5 g) with warming, and thereto were added isopropyl myristate (10 g), polyoxyethylene lauryl ether (1.5 g), a 4% aqueous solution of carboxyvinyl polymer (Carbopol 940) (25 g), purified water (43 g) and a 1% aqueous solution of sodium edetate (1.2 g). The mixture was heated at about 70° to 80° C. on a water bath, and thereto was added with stirring a 2% aqueous solution of sodium hydroxide (3 g), and further added purified water to make 100 g in total. After stirring well, the mixture was cooled to give a creamy preparation having a viscosity of 76,000 cps and a pH of 6.10.

EXAMPLE 11

Clotrimazole (1 g) was dissolved in crotamiton (5 g) at about 70° C., and thereto were added isopropyl myristate (10 g), polyoxyethylene lauryl ether (1.5 g), a 4% aqueous solution of carboxyvinyl polymer (Carbopol 940) (10 g), purified water (50 g) and a 1% aqueous solution of sodium edetate (1.2 g). The mixture was heated at about 70° to 80° C. on a water bath, and thereto was added with stirring a 10% aqueous solution of sodium hydroxide (1.6 g) and further added purified water to make 100 g in total. After stirring well, the mixture was cooled to give a creamy preparation having a viscosity of 22,000 cps and a pH of 7.20.

EXAMPLE 12

Clotrimazole (0.5 g) was dissolved in crotamiton (2 g) at about 70° C., and thereto were added liquid paraffin (5.0 g), stearyl alcohol (10 g), propylene glycol (10 g), polyoxyethylene cetyl ether (1.5 g), a 4% aqueous solution of carboxyvinyl polymer (Carbopol 940) (20 g), and purified water (40 g). The mixture was heated at about 70° to 80° C. on a water bath to dissolve completely stearyl alcohol, and thereto was added with stirring a 10% aqueous solution of sodium hydroxide (9 g), and further added purified water to make 100 g in total. After stirring well, the mixture was cooled to give a creamy preparation having a viscosity of 75,000 cps and a pH of 8.20.

EXAMPLE 13

Clotrimazole (2 g) was dissolved in crotamiton (8 g) at about 70° C., and thereto were added liquid paraffin (10 g), propylene glycol (10 g), polyoxyethylene sorbitan monolaurate (1 g), a 4% aqueous solution of carboxyvinyl polymer (Carbopol 940) (8 g), a purified water (60 g) and a 1% aqueous solution of sodium edetate (1.2 g). The mixture was heated at about 70° to 80° C. on a water bath, and thereto was added with continuously stirring a 2% aqueous solution of sodium hydroxide (6.4 g), and further added purified water to make 100 g in total. After stirring well, the mixture was cooled to give a creamy preparation having a viscosity of 13,000 cps and a pH of 6.73.

EXAMPLE 14

Clotrimazole (1 g) was dissolved with stirring in crotamiton (4 g) at about 70° to 80° C., and thereto added with stirring ethanol (40 g), and further was gradually added water to make 100 g in total to give a colorless, transparent liquid preparation.

EXAMPLE 15

Clotrimazole (0.5 g) was dissolved with stirring in crotamiton (2.0 g) at about 70° to 80° C., and thereto was gradually added with stirring ethanol (40 g), and further added with stirring purified water to make 100 g in total to give a colorless, transparent liquid preparation.

EXAMPLE 16

Clotrimazole (2 g) was dissolved in crotamiton (8 g) at about 70° to 80° C., and thereto was gradually added with stirring ethanol (40 g), and further was gradually added purified water to make 100 g in total to give a colorless, transparent liquid preparation.

EXAMPLE 17

Clotrimazole (1 g) was dissolved in crotamiton (4 g) at about 70° to 80° C., and thereto were gradually added with stirring ethanol (30 g) and propylene glycol (10 g), and further added purified water to make 100 g in total to give a colorless, transparent liquid preparation.

What is claimed is:

1. A preparation useful for external treatment of trichophytoses, which comprises a solution of clotrimazole in crotamiton in admixture with a carrier or diluent, wherein said clotrimazole is contained in an amount of 0.5 to 2% by weight and said crotamiton is contained in an amount of 2 to 10% by weight, based upon the total weight of the preparation.

2. A gel preparation useful for external treatment of trichophytoses, which comprises 0.5 to 2.0% by weight of clotrimazole, 2 to 10% by weight of crotamiton, 30 to 70% by weight of ethanol or ethanol containing less than 40% by weight of propylene glycol, 0.1 to 3.0% by weight of carboxyvinyl polymer, and remainder of water, said preparation having been neutralized with a basic substance and having a pH of 4 to 10 and a viscosity of 2,000 to 100,000 cps at 20° C.

3. A gel preparation according to claim 2, wherein the carboxyvinyl polymer is contained in an amount of 0.5 to 1.2% by weight.

4. A creamy preparation useful for external treatment of trichophytoses, which comprises 0.5 to 2.0% by weight of clotrimazole, 2 to 10% by weight of crotamiton, 10 to 50% by weight of an oily substance, 0.5 to 5.0% by weight of a nonionic surfactant, 0.1 to 3.0% by weight of a carboxyvinyl polymer, and remainder of water, said preparation having been neutralized with basic substance and having a pH of 4 to 10 and a viscosity of 10,000 to 100,000 cps at 20° C.

5. A creamy preparation according to claim 4, wherein the carboxyvinyl polymer is contained in an amount of 0.5 to 1.2% by weight.

6. A creamy preparation according to claim 4, wherein the oily substance is a member selected from the group consisting of a fatty alcohol having 8 to 18 carbon atoms, a fatty acid having 8 to 18 carbon atoms, an alkyl ester of a fatty acid wherein the alkyl moiety has 1 to 18 carbon atoms and the fatty acid has 8 to 18 carbon atoms, a liquid or solid hydrocarbon, and a fat and oil.

7. A creamy preparation according to claim 4, wherein propylene glycol is incorporated in an amount of less than 40% by weight based upon the total weight of the preparation.

8. A liquid preparation useful for external treatment of trichophytoses which comprises 0.5 to 2% by weight of clotrimazole, 2 to 10% by weight of crotamiton, 30 to 60% by weight of ethanol or ethanol containing less than 40% by weight of propylene glycol, and remainder of water.

9. A pharmaceutical composition containing a solution of clotrimazole in crotamiton in an amount effective for the external treatment of trichophytoses.

10. The composition of claim 1 in the form of a gel, a creamy preparation or an aqueous solution containing ethanol.

11. A process for preparing a transparent gel preparation useful for external treatment of trichophytoses, which comprises dissolving clotrimazole in crotamiton, adding thereto ethanol or ethanol containing less than 40% by weight of propylene glycol and an aqueous solution of a carboxyvinyl polymer, and then neutralizing the mixture with a basic substance to a pH of 4 to 10, said gel preparation comprising 0.5 to 2.0% by weight of clotrimazole, 2 to 10% by weight of crotamiton, 30 to 70% by weight of ethanol or propylene glycol-containing ethanol, 0.1 to 3.0% by weight of the carboxyvinyl polymer, and remainder of water, and having a pH of 4 to 10 and a viscosity of 2,000 to 100,000 cps at 20° C.

12. A process for preparing a creamy preparation useful for external treatment of trichophytoses, which comprises dissolving clotrimazole in crotamiton, adding thereto an oily substance, a nonionic surfactant and an aqueous solution of a carboxyvinyl polymer, and neutralizing the mixture with a basic substance to a pH of 4 to 10, said creamy preparation comprising 0.5 to 2.0% by weight of clotrimazole, 2 to 10% by weight of crotamiton, 10 to 50% by weight of the oily substance, 0.5 to 5.0% by weight of the nonionic surfactant, 0.1 to 3.0% by weight of the carboxyvinyl polymer and remainder of water, and having a pH of 4 to 10 and a viscosity of 10,000 to 100,000 cps at 20° C.

13. A process for preparing a liquid preparation useful for external treatment of trichophytoses, which comprises dissolving clotrimazole in crotamiton, adding thereto ethanol or ethanol containing less than 40% by weight of propylene glycol and water, said liquid preparation comprising 0.5 to 2.0% by weight of clotrimazole, 2 to 10% by weight of crotamiton, 30 to 60% by weight of ethanol or propylene glycol-containing ethanol, and remainder of water.

* * * * *